United States Patent
Hearn et al.

(10) Patent No.: US 8,011,785 B2
(45) Date of Patent: Sep. 6, 2011

(54) OPTICAL ALIGNMENT APPARATUS AND METHOD THEREFOR

(75) Inventors: Austen Hearn, Reading (GB); Simon Meadowcroft, Stowmarket (GB); Richard Holley, Maidenhead (GB)

(73) Assignee: Lein Applied Diagnostics, Berkshire (GB)

( * ) Notice: Subject to any disclaimer, the term of this patent is extended or adjusted under 35 U.S.C. 154(b) by 0 days.

(21) Appl. No.: 12/671,126

(22) PCT Filed: Jul. 29, 2008

(86) PCT No.: PCT/GB2008/050634
§ 371 (c)(1),
(2), (4) Date: May 10, 2010

(87) PCT Pub. No.: WO2009/016403
PCT Pub. Date: Feb. 5, 2009

(65) Prior Publication Data
US 2010/0220289 A1    Sep. 2, 2010

(30) Foreign Application Priority Data
Jul. 30, 2007  (GB) .................................. 0714736.6

(51) Int. Cl.
*A61B 3/14* (2006.01)
*A61B 3/10* (2006.01)
(52) U.S. Cl. ......... 351/208; 351/211; 351/214; 351/206
(58) Field of Classification Search ........... 351/200–246
See application file for complete search history.

(56) References Cited

U.S. PATENT DOCUMENTS

| | | | |
|---|---|---|---|
| 4,407,008 A | 9/1983 | Schmidt et al. | |
| 4,768,874 A | 9/1988 | Webb et al. | |
| 4,806,004 A | 2/1989 | Wayland | |
| 5,212,505 A | 5/1993 | Penney | |
| 5,239,178 A | 8/1993 | Derndinger et al. | |
| 5,280,313 A * | 1/1994 | Kohayakawa | 351/211 |
| 5,341,180 A * | 8/1994 | Isogai et al. | 351/206 |
| 5,463,430 A * | 10/1995 | Isogai et al. | 351/208 |
| 5,785,651 A | 7/1998 | Kuhn et al. | |
| 5,984,474 A | 11/1999 | Schweitzer | |
| 6,181,957 B1 | 1/2001 | Lambert et al. | |
| 6,226,089 B1 | 5/2001 | Hakamata | |

(Continued)

FOREIGN PATENT DOCUMENTS

DE    196 32 594 A1    2/1998

(Continued)

OTHER PUBLICATIONS

PCT Search Report for PCT/GB2008/050634; May 20, 2009.
Masters, Barry R. and Bohnke, Matthias; "Three-Dimensional Confocal Microscopy of the Living Human Eye"; 2002; vol. 4, pp. 69-91; Annual Review of Biomedical Engineering (28 pages).

(Continued)

*Primary Examiner* — Mohammed Hasan
(74) *Attorney, Agent, or Firm* — Bracewell & Giuliani LLP

(57) ABSTRACT

An optical measurement apparatus comprises an optical system. The optical system comprises a source and an image capture device. The source is arranged to generate, when in use, a beam of electromagnetic radiation. Further, the optical system is arranged to direct the beam of electromagnetic radiation to a location to be measured. The optical measurement apparatus also comprises a feedback arrangement arranged to receive a reflected beam from the location to be measured and to provide feedback information in response to receipt of the reflected beam, the feedback information being indicative of degree of alignment of the location to be measured with the optical system.

17 Claims, 8 Drawing Sheets

U.S. PATENT DOCUMENTS

| | | | |
|---|---|---|---|
| 6,382,794 | B1 | 5/2002 | Lai et al. |
| 6,424,850 | B1 | 7/2002 | Lambert et al. |
| 6,574,501 | B2 | 6/2003 | Lambert et al. |
| 6,836,337 | B2 | 12/2004 | Cornsweet |
| 7,731,361 | B2 * | 6/2010 | Honda .......................... 351/211 |
| 2004/0080759 | A1 | 4/2004 | Shaver |
| 2004/0257585 | A1 | 12/2004 | Cornsweet |

FOREIGN PATENT DOCUMENTS

| | | |
|---|---|---|
| EP | 0 485 803 A1 | 5/1992 |
| EP | 0 810 457 A1 | 12/1997 |
| JP | 3-55510 A | 3/1991 |
| WO | WO 92/22793 A | 12/1992 |
| WO | WO 93/07801 A | 4/1993 |
| WO | 2004/034894 A1 | 4/2004 |

OTHER PUBLICATIONS

Li, Jie; Jester, James V.; Cavanagh, Dwight; Black, Truman D. and Petroll, W. Matthew; "On-Line 3-Dimensional Confocal Imaging in Vivo"; Sep. 2000, vol. 41, No. 10; pp. 2945-2953; Investigative Ophthalmology & Visual Science (9 pages).

Li, Hong Fang; Petroll, W. Matthew; Moller-Pedersen, Torben; Maurer, James K.; Cavanagh, H. Dwight; and Jester, James V.; Epithelial and Corneal Thickness Measurements by in vivo Confocal Microscopy Through Focusing (CMTF); May 31, 1996; Oxford University Press pp. 214-221; (8 pages).

McLaren, Jay W., PhD.; Nau, Cherie B., BS; Erie, Jay C., MD; and Bourne, William M., MD; "Corneal Thickness Measurement by Confocal Microscopy, Ultrasound, and Scanning Slit Methods"; Jun. 2004; American Journal of Ophthalmology; pp. 1011-1020; Feb. 2005; vol. 139, No. 2, pp. 391-392 (12 pages).

* cited by examiner

OPTICAL ALIGNMENT APPARATUS AND METHOD THEREFOR

RELATED APPLICATION

This application claims priority to PCT application PCT/GB2008/050634 filed Jul. 29, 2008, which claimed priority to British patent application GB 0714736.6 filed Jul. 30, 2007.

BACKGROUND OF THE INVENTION

The present invention relates to an optical alignment apparatus of the type that, for example, is used to provide alignment with a location having a physiological property to be measured, such as with respect to an eye. The present invention also relates to a method of providing optical alignment with a location having a physiological property to be measured, such as with respect to an eye.

Diabetes is a major and rapidly growing problem with over 230 million people suffering from the disorder worldwide. In addition, studies have shown that the incidence of juvenile-onset, insulin-dependent diabetes has doubled over the last 15 years. There has also been a five fold increase in the number of children under the age of 5 suffering from diabetes in just 20 years.

The symptoms associated with diabetes can be severe. If the blood glucose level is not suitably controlled by the patient, the physical damage which may be caused includes blindness, heart disease and gangrene. As such, the mortality rate for people with diabetes is significantly higher than the rate for the average person.

A person's blood glucose concentration varies over a relatively short timescale, due to a number of factors, such as the length of time since the patient's last meal, the type of food ingested, the amount of exercise taken, and whether or not the patient is otherwise ill. As a result, people with diabetes usually need to test their glucose levels many times a day, in order to monitor and control their condition. The actual testing regime varies between patients and is individually prescribed by the doctor or diabetes educator of the patient.

The primary method used for testing blood glucose concentration involves the taking of a blood sample, which is then analysed. In this test, a patient's finger or arm is pricked with a small needle and the resulting drop of blood is placed on a test strip, for analysis in a hand-held meter. If the glucose concentration reading is above an acceptable level, insulin must be injected to bring the glucose concentration back within an acceptable range.

Due to the frequency of testing required to monitor the blood glucose concentration, the patient is normally expected to perform the tests throughout the day, drawing and analysing the blood sample himself. There are a number of problems experienced by patients with the above procedure. Firstly, the technique is invasive and therefore carries the risk of infection. Secondly, continual pricking of the fingers causes hard skin. Thirdly, the process is clearly not pain-free. Finally, there is a large, ongoing consumables cost associated with this method. As a result of these and other problems, certain sectors of the diabetic population do not test themselves as often as required. This is particularly the case for the elderly, who tend to lack the fine motor skills required; teenagers, who tend to find the whole procedure socially embarrassing; and children, who tend not to accept the discomfort associated with the process.

A number of non-invasive blood glucose concentration measuring techniques have been proposed to overcome these problems. In general these have been designed to work by making a measurement through the skin but the variability in the skin's characteristics have led to inaccurate results.

More recently the eye has been proposed as a better measurement location. Possible techniques for measuring glucose in the eye include spectroscopy on the conjunctiva (e.g. U.S. Pat. No. 6,975,892), psychophysical measurements on the fundus (e.g. U.S. Pat. No. 6,895,264), a contact lens or other implantable device that absorbs glucose (e.g. U.S. Pat. No. 6,980,842 or US 2006/0166350) or a measurement of the ocular refractive correction (e.g. U.S. Pat. No. 6,442,410).

One particular approach which has been suggested involves measuring the glucose concentration of the aqueous humour in the anterior chamber of the eye, since, while varying between individuals, there is a close correlation between this concentration and the blood glucose concentration. Measurement of the glucose concentration of the aqueous humour may be achieved by various means; for example, by polarimetry (e.g., U.S. Pat. No. 5,896,198); by Raman techniques (e.g., WO A 00/02479); by fluorescence photometry (e.g., WO 2005/120334); by spectrometry (e.g., U.S. Pat. No. 5,969,815); by fluorescence spectroscopy (e.g., WO 02/087429) or by reflectometry (e.g., U.S. Pat. No. 6,236,089).

A desirable alternative approach to measuring the glucose concentration in the aqueous humour involves measuring the refractive index of the aqueous humour, since there is a strong correlation between the refractive index and the glucose concentration. In this respect, U.S. Pat. No. 3,963,019, U.S. Pat. No. 6,152,875, WO 03/025562, WO 05/044099 and WO 05/058152 describe various techniques associated with measurement of the refractive index of the aqueous humour.

In addition there are many other measurements that require an instrument to be aligned to the eye of a patient or operator. In one example, it is necessary to measure the thickness or shape of the cornea in order to make Laser-Assisted in Situ Keratomileusis (LASIK) surgery safer (for example as described in U.S. Pat. No. 6,585,723 and US 2004/0080759).

In all of the above cases, the measurement fidelity is compromised by variations in alignment between the meter and the patient's eye. In addition, for a successful personal use meter, it is important that the patient is able to use the meter by themselves, and align to the meter by themselves, without any clinician involvement.

Furthermore, at times it is not always possible to achieve good alignment to the eye when measuring glucose levels and other parameters of the eye non-invasively.

SUMMARY OF THE INVENTION

According to a first aspect of the present invention, there is provided a confocal measurement apparatus comprising: an optical system comprising: a source arranged to emit, when in use, a probe beam, the optical system being arranged to direct, when in use, the probe beam to a location to be measured; an apertureless detector arrangement capable of receiving a reflected beam from the location to be measured, the apertureless detector arrangement comprising a plurality of detector elements; and a processing resource operably coupled to the apertureless detector arrangement; wherein the processing resource is arranged to identify, when in use, a number of the plurality of detector elements illuminated by the reflected beam and select a detector element from the number of the plurality of detector elements based upon a predetermined criterion for performing a calculation in relation to an output signal generated by the selected detector element.

The criterion may be maximum luminous intensity. The criterion may be luminous intensity in excess of a predetermined luminous intensity threshold. The criterion may be movement of illumination of detector elements with respect to time.

The calculation in relation to the output signal may be a calculation of degree of misalignment of the location to be measured with a receiving axis of the optical system.

The optical system may have a receiving axis; and the selection of the number of the plurality of detector elements may serve to compensate for off-axis propagation of the reflected beam with respect to the receiving axis as a result of misalignment of the location to be measured with the optical system.

According to a second aspect of the present invention, there is provided a method of confocal measurement, comprising: emitting a probe beam; directing the probe beam to a location to be measured; receiving at an apertureless detector a reflected beam from the location to be measured, the apertureless detector comprising a plurality of detector elements; identifying a number of the plurality of detector elements illuminated by the reflected beam; and selecting a detector element from the number of the plurality of detector elements based upon a predetermined criterion for performing a calculation in relation to an output signal generated by the selected detector element.

According to a third aspect of the present invention, there is provided a confocal measurement apparatus comprising: an optical system comprising: a source arranged to emit, when in use, a probe beam, the optical system being arranged to direct, when in use, the probe beam to a location to be measured; an apertureless detector arrangement capable of receiving a reflected beam from the location to be measured, the apertureless detector arrangement comprising a plurality of detector elements; and a processing resource operably coupled to the apertureless detector arrangement; wherein the processing resource is arranged to identify, when in use, a number of the plurality of detector elements illuminated by the reflected beam and evaluate luminous intensity in respect of the number of the plurality of detector elements.

The evaluation of the luminous intensity may be calculation of an average luminous intensity value in respect of the number of the plurality of detector elements.

The average value may be generated with respect to a spatial dimension of the apertureless detector arrangement.

The evaluation may be integrating the number of the plurality of detector elements. The number of the plurality of detector elements may be integrated over time.

The number of the plurality of detector elements may be identified based upon a predetermined criterion. The criterion may be illumination intensity above a predetermined luminous intensity threshold.

The optical system may be arranged to direct the probe beam to a plurality or continuum of measurement locations comprising the location to be measured.

A physiological body-part may comprise the location to be measured. The physiological body-part is an eye.

According to a fourth aspect of the present invention, there is provided a method of confocal measurement, comprising: emitting a probe beam; directing the probe beam to a location to be measured; receiving at an apertureless detector a reflected beam from the location to be measured, the apertureless detector comprising a plurality of detector elements; identifying a number of the plurality of detector elements illuminated by the reflected beam; and evaluating luminous intensity in respect of the number of the plurality of detector elements.

According to a fifth aspect of the present invention, there is provided an optical measurement apparatus comprising: an optical system comprising: a source arranged to generate, when in use, a beam of electromagnetic radiation, the optical system being arranged to direct, when in use, the beam of electromagnetic radiation to a location to be measured; and a feedback arrangement arranged to receive, when in use, a reflected beam from the location to be measured and to provide feedback information in response to receipt of the reflected beam, the feedback information being indicative of degree of alignment of the location to be measured with the optical system.

The location to be measured may be a location of a feature of an eye; the optical system may be arranged to receive the reflected beam from the eye; and the optical system may be further arranged to direct at least part of the reflected beam back to the eye, the redirected reflected beam constituting the feedback information. The beam of electromagnetic radiation may comprise an alignment image, the reflected beam also comprising the alignment image.

The reflected image may originate from a cornea of the eye. The reflected image may originate from a lens of the eye. The reflected image may originate from a retina of the eye. The reflected image may be a Purkinje image.

The optical source may be arranged to generate a plurality of images with respect to a vanishing point, the optical system being further arranged to direct, when in use, the plurality of images to the eye for alignment thereof. The feedback arrangement may comprise a processing resource operably coupled to an image capture device in order to generate the feedback information in response to receipt of the reflected beam relative to a predetermined axis, the predetermined axis corresponding to an aligned state.

The location to be measured may be a location of a feature of an eye; and the feedback arrangement may be arranged to determine, when in use, a location of the feature of the eye relative to the optical system. The optical system may have a receiving axis constituting the predetermined axis; and the processing resource may be arranged to provide the feedback information as an indication of the degree of alignment of the location of the feature of the eye with the receiving axis.

The feedback arrangement may comprise a processing resource operably coupled to an image capture device; the optical system may have a receiving axis; the location to be measured may be coaxial with a first axis of an eye, the eye having a second axis; and the processing resource may be arranged to provide feedback for obtaining a misalignment of the first axis with the receiving axis in order to achieve alignment of the second axis with the receiving axis.

The receiving axis may extend from the image capture device.

The feedback information may be an audible or visual indication of alignment.

The source may be capable of emitting a measurement probe beam invisible to an eye.

The source may be arranged to generate a measurement probe beam, the optical system being arranged to direct, when in use, the measurement probe beam to the location to be measured; and the apparatus may further comprise: a detector arranged to receive, when in use, a reflected measurement probe beam from the location to be measured. The measurement probe beam may also serve as the beam of electromagnetic radiation.

The feedback arrangement may comprise a processing resource operably coupled to an image capture device, the processing resource being arranged to generate a first measure of a first characteristic corresponding to illumination of the image capture device, the first measure constituting the feedback information. The processing resource may be arranged to generate a second measure of a second characteristic corresponding to illumination of the image capture device, the second measure being of a different type to the first measure.

The first measure may comprise a qualitative measure of the first characteristic and/or the second measure may be a qualitative measure of the second characteristic.

The first measure may comprise a quantitative measure of the first characteristic and/or the second measure may be a quantitative measure of the second characteristic.

The apparatus may further comprise a store for storing characteristic data relating to illumination and corresponding to a state of substantially optimum alignment with the optical system.

The apparatus may further comprise a store for storing characteristic data relating to illumination and corresponding to a state of mis-alignment with the optical system.

The processing resource may be arranged to compare the feedback information with the characteristic data stored in order to determine alignment or misalignment of the location to be measured with the optical system.

A physiological body-part may comprise the location to be measured. The physiological body-part may be an eye.

According to a sixth aspect of the present invention, there is provided a method of optical measurement, comprising: generating a beam of electromagnetic radiation; directing the beam of electromagnetic radiation to a location to be measured; receiving via an optical system a reflected beam from the location to be measured; and providing feedback information in response to receipt of the reflected beam, the feedback information being indicative of degree of alignment of the location to be measured with the optical system.

According to a seventh aspect of the present invention, there is provided an optical alignment apparatus comprising: an optical system comprising: a source arranged to generate, when in use, a first alignment image and a second alignment image, the optical system being arranged to direct, when in use, the first and second images to an image plane for aligning a location of a feature of an eye to be measured; wherein the first and second alignment images are arranged so as to appear spatially separated when the eye is unaligned with the optical system and to appear at intended relative positions when the eye is aligned with the optical system.

The optical system may have a receiving axis; and the first and second alignment images may be arranged so as to appear spatially separated when the eye is unaligned with the receiving axis and to appear at intended relative positions when the eye is aligned with the receiving axis.

The intended relative positions may correspond to the first and second alignment images being superimposed.

The first and second alignment images may be incomplete parts of an image, the intended relative positions corresponding to the first and second alignment images appearing in combination so as to complete the image.

The apparatus may further comprise a processing resource operably coupled to the source in order to control the spatial separation of the first and second alignment images.

The spatial separation of the first and second alignment images may be adaptable in order to align an axis of the eye with the optical system. The axis of the eye may be an optical axis of the eye. The axis of the eye may be a visual axis of the eye.

An appearance of the first alignment image may be changeable and/or an appearance of the second alignment image may be changeable.

The optical system may provide the first alignment image as a static image; the apparatus may further comprise a display device capable of movably displaying the second alignment image so as to vary the spatial separation between the first and second alignment images.

The optical system may be arranged to provide a folded path for the second alignment image.

The first alignment image may be presented so as to cause the eye to unaccommodate and/or the second alignment image may be presented so as to cause the eye to unaccommodate.

The first alignment image may be presented so as to have an apparent object distance constituting infinity in order to cause the eye to unaccommodate and/or the second alignment image may be presented so as to have an apparent object distance constituting infinity in order to cause the eye to unaccommodate.

The first alignment image may be presented so as to control an amount of accommodation of the eye and/or the second alignment image may be presented so as to control an amount of accommodation of the eye.

The source may be arranged to emit, when in use, a measurement probe beam, the measurement probe beam comprising the first alignment image.

A physiological body-part may comprise the location to be measured.

According to a eighth aspect of the present invention, there is provided a method of optical alignment, comprising: generating a first alignment image and a second alignment image; directing the first and second alignment images to an image plane for aligning a location of a feature of an eye to be measured; and providing the first and second alignment images so as to appear spatially separated when the eye is unaligned with the optical system and to appear at intended relative positions when the eye is aligned with the optical system.

According to a ninth aspect of the present invention, there is provided a computer program element comprising computer program code means to make a computer execute the method as set forth above in relation to any one of the second, fourth, sixth or eighth aspects of the invention.

The computer program element may be embodied on a computer readable medium.

It is thus possible to provide an apparatus and method that enables an optical system of a confocal or non-confocal measurement apparatus to be aligned with a location to be measured, for example a surface of an eye, to determine the concentrations of other compounds in the eye, including both naturally occurring and intentionally introduced chemicals, and which can be used to measure other properties of the eye, such as the location of each surface or the thickness or location of the constituent elements of the eye or medical conditions visible in the eye.

BRIEF DESCRIPTION OF THE DRAWINGS

At least one embodiment of the invention will now be described, by way of example only, with reference to the accompanying drawings, in which.

DETAILED DESCRIPTION OF THE EXEMPLARY EMBODIMENTS

Figure 1:
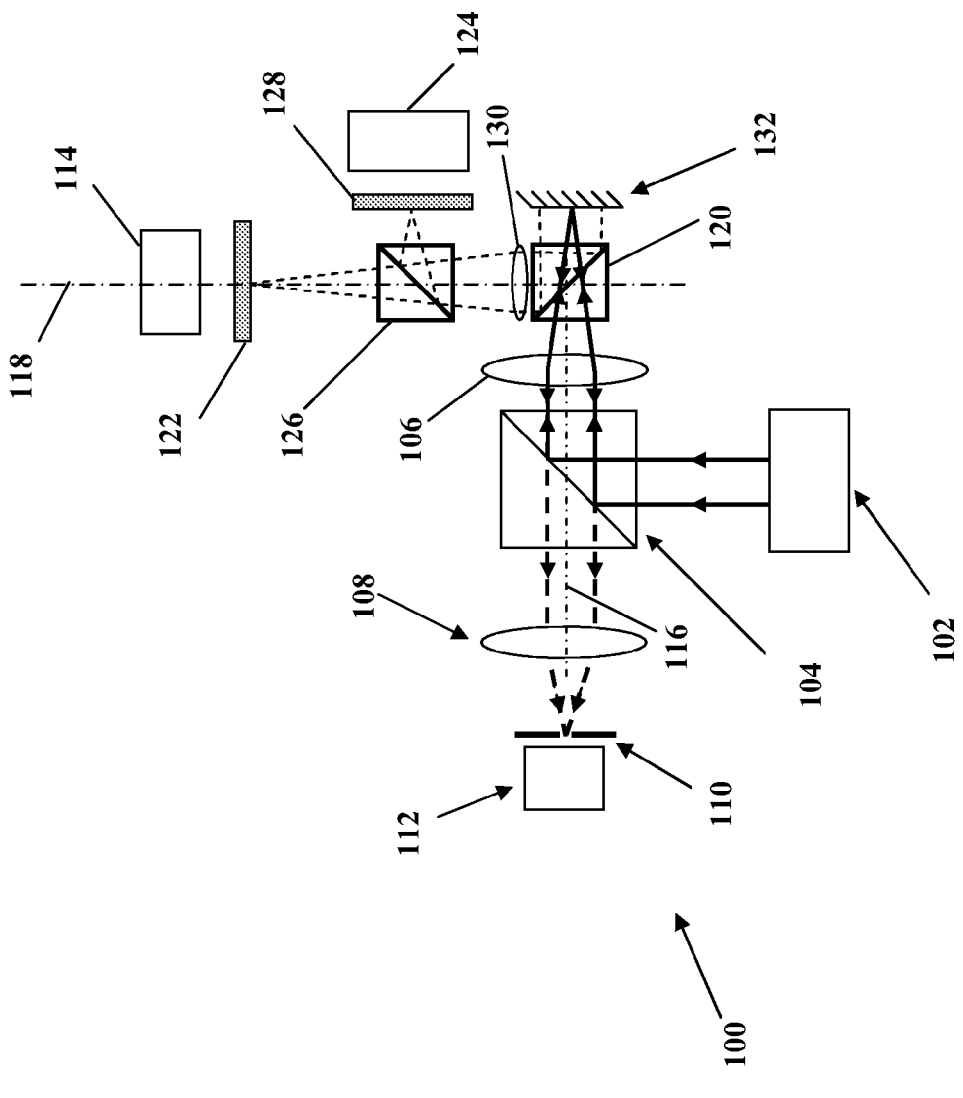
FIG. 1 is a schematic diagram of an apparatus constituting an embodiment of the invention.

Throughout the following description identical reference numerals will be used to identify like parts.

Referring to FIG. 1, an optical measurement apparatus, for example a glucometer, comprises an optical system 100 including a first source 102 of electromagnetic radiation, for example visible light, though light invisible to the eye, for example near infra-red light, can be used so as to reduce discomfort when a measurement is to be made in relation to an eye. An output window (not shown) of the first source 102 is oriented towards a first beamsplitter 104 that is placed in an optical path of the first source 102. The first beamsplitter 104 serves to fold the optical path of the first source 102 towards a scanning lens 106. In this example, the scanning lens 106 is shown as a single lens, though the skilled person will appreciate a lens system can serve as the scanning lens 106 or any other suitable optical arrangement, scanning or non-scanning in nature for making measurements. The scanning lens 106 is capable of linearly translating so as to move optically closer to or further from a location to be measured 132 in accordance with UK patent publication no. GB-B-2 407 378 or GB-A-2 209 033 where a measurement probe beam emitted by the first source is directed to a plurality or continuum of measurement locations comprising the location to be measured 132. The first beamsplitter 104 is a half-silvered mirror, though the skilled person will appreciate that any suitable alternative optical element or arrangement can be employed to function as the beamsplitter 104, for example a polarising beamsplitter and ¼ wave plate disposed between the polarising beam splitter and the scanning lens 106.

A first focussing lens 108 is disposed opposite the first beamsplitter 104 so that the first beamsplitter 104 is located between the scanning lens 106 and the first focussing lens 108. As the optical measurement apparatus is a confocal system, an aperture 110 constituting a pinhole is disposed opposite the first focussing lens 108, a detector 112 being disposed adjacent the aperture 110. The detector 112, in this example, comprises a photodiode (not shown in FIG. 1).

A second source 114 is placed away from the optical receiving axis 116 of the optical system 100. In this example, the second source 114 is aligned with a tangential alignment axis 118 that meets the optical axis 116 at a second beamsplitter 120. However, other, non-tangential, alignment axes can be employed instead of the tangential alignment axis 118, for example a Brewster alignment axis. A first graticule 122 is disposed in front of the second source 114. Similarly, a third source 124 is disposed perpendicularly with respect to the tangential alignment axis 118 and directed at a third beamsplitter 126 disposed in the tangential alignment axis 118 between the second beamsplitter 120 and the first graticule 122. A second graticule 128 is disposed between the third source 124 and the third beamsplitter 126. A second focussing lens 130 is also placed in the tangential alignment axis 118 adjacent the second beamsplitter 120. The skilled person will again appreciate that the second focussing lens 130 can be any suitable lensing arrangement to generate a nominally parallel beam at the location to be measured 132.

The first and second graticules 122, 128 are configured so as to define respective shapes, for example cross-hairs or circles of the same or differing sizes.

Figure 2:
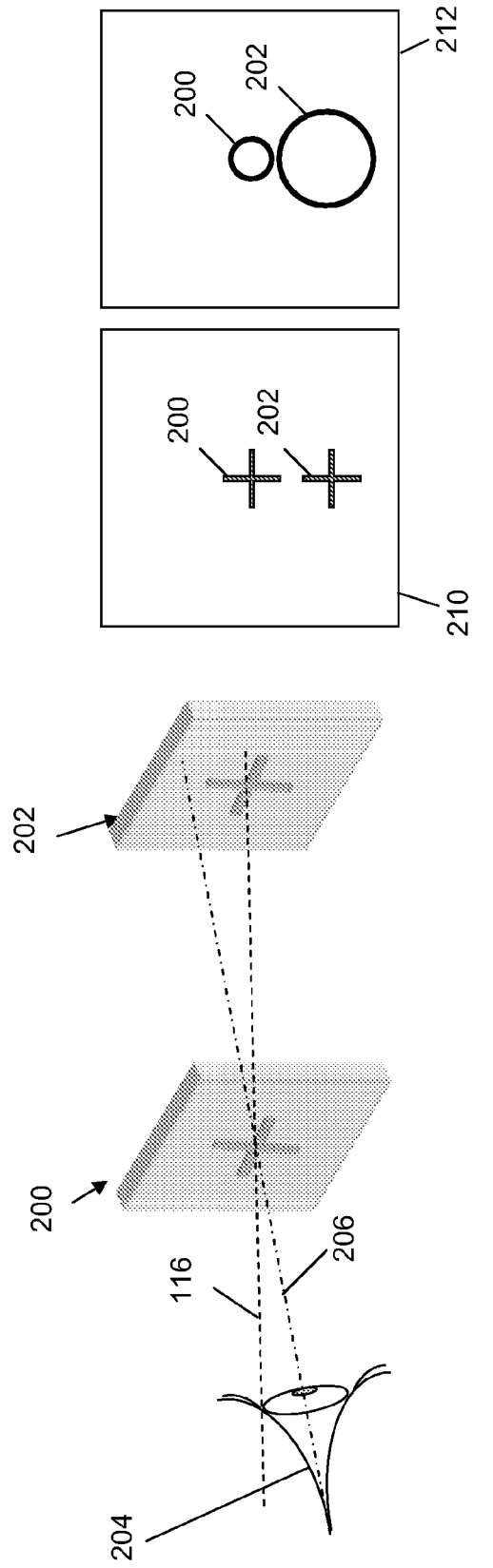
FIG. 2 is a schematic diagram of alignment marker images generated by the apparatus of FIG. 1 and in a mis-aligned state.

Referring to FIG. 2, the skilled person will appreciate that the first and second graticules 122, 128 can be a first display device and a second display device, the first display device being capable of generating a first alignment marker image 200 and the second display device being capable of generating a second alignment marker image 202 to be viewed by an eye 204. In particular, the eye 204 has a first axis 206, for example an optical axis, to be aligned with the optical receiving axis 116 of the optical system 100. In this example, the first display device is a first Liquid Crystal Display (LCD) device and the second display device is a second LCD device. However, the skilled person will appreciate that other imaging devices can be employed, for example one or more Spatial Light Modulators (SLMs). The second and third sources 114, 124 and the first and second graticules 122, 128 constitute a source of the first and second alignment marker images 200, 202.

Instead of using separate display devices dedicated to generation of the first and second alignment marker images 200, 202, a single functionally partitioned imaging device can be employed, for example by dividing a single imaging device into two functional halves: one half responsible for generating the first alignment marker image 200 and the second half responsible for generating the second alignment marker image 202 and having a lensing arrangement disposed adjacent thereto in order to provide an appearance of spatial separation to the eye 204 between the first and second alignment marker images 200, 202.

Although not implemented in this example, the first and second display devices can be arranged so that, for example, the first alignment marker image 200 is focussed so as to have an apparent object distance of infinity and the second alignment marker image 202 is focussed much closer to the eye 204. For practical purposes, the first alignment marker image 200 is at an apparent object distance of about 6 meters. The purpose of the much longer apparent object distance is to cause the eye 204 to unaccommodate, which can be a requirement for some measurements. Indeed, if desired, the apparent object distance can be controlled in order to achieve a required amount of accommodation of the eye.

Although two alignment marker images are employed in this example, a greater number of alignment marker images can be employed. In another embodiment, the first and second alignment marker images 200, 202 can be configured as an aperture and a mark. Hence, for example, the first alignment marker image 200 can be circularly shaped and the second alignment marker image 202 can be a cross, or other mark, so as to provide an impression to a patient that the cross is being viewed through an aperture (the circularly shaped first alignment marker image 200). In this respect, the first alignment marker image 200 can be formed by an opaque screen having a light-transmissive aperture; the light-transmissive aperture can thus serve as a port through which to view the second alignment marker image 202 and hence align the first and second alignment marker images 200, 202.

In this example, the first alignment marker image 200 is generated so as to appear at a first focal distance from the eye 204 and the second marker image 200 is generated so as to appear at a second focal distance from the eye 204, the first and second marker images 200, 202 appearing superimposed when viewed along the optical receiving axis 116 of the optical system 100. A microprocessor (not shown in FIG. 1)

can be coupled to the second and/or third sources 114, 124 in order to control a spatial separation between the first and second alignment marker images 200, 202. In this respect, the spatial separation between the first and second alignment marker images 200, 202 can be configured in order to align different axes of the eye to the optical receiving axis 116, depending upon the location to be measured 132, for example the optical axis or the visual axis of the eye.

In operation, the second and third sources 114, 124 emit light that passes through the first and second graticules 122, 128 or display devices respectively to provide a first image beam and a second image beam which are incident upon the third beamsplitter 126 and combined before passing through the second focussing lens 130. Thereafter, the combined beams are directed by the second beamsplitter 120 to the location to be measured 132 (FIG. 1) in, in this example, the eye 204 (FIG. 2). The first alignment marker image 200 is generated so as to appear at a first focal distance from the eye 204 and the second marker image 200 is generated so as to appear at a second focal distance from the eye 204, the first and second alignment marker images 200, 202 appearing superimposed or coaxial when viewed along the optical receiving axis 116 of the optical system 100.

A first axis 206 of the eye 204 is typically initially not aligned with the optical receiving axis 116 of the optical system 100. Consequently, a field of view 210 of the eye 204 sees the first and second marker images 202, 202 spatially separated from each other as a result of parallax.

If the eye 204 is then moved (FIG. 3), for example by moving the head and/or the eye 204 in its socket, in an attempt to cause the first and second alignment images 200, 202 to become superimposed, the first axis 206 of the eye 204 becomes aligned with the optical receiving axis 116 of the optical system 100. In this respect, one of the first and second alignment marker images 200, 202 can be stationary so as to serve, for example, as a reference and another of the first and second alignment marker images 200, 202 can appear to move in response to movement of the eye 204 relative to the optical receiving axis 116.

Once aligned, a measurement can be made in respect of the location 132, now aligned with the optical receiving axis 116 of the optical system 100 in accordance, for example, with the techniques set forth in UK patent publication nos. GB-B-2 407 378 and GB-A-2 409 033. In some embodiments, it can be desirable to use a probe beam for measurement purposes to additionally bear the first alignment marker image 200 and/or the second alignment marker image 202.

Figure 3:
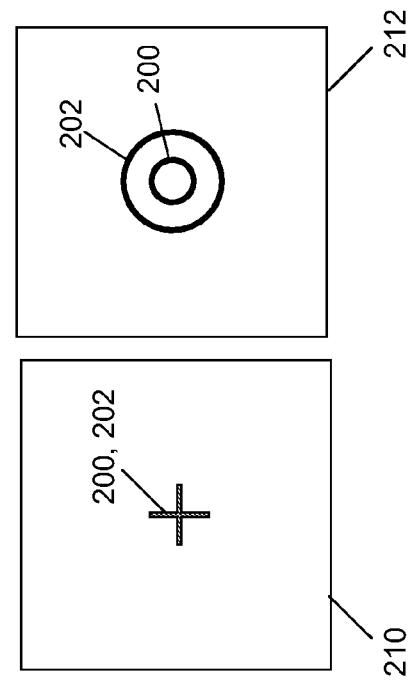
FIG. 3 is a schematic diagram of the alignment marker images of FIG. 2 when viewed in an aligned state.
Figure 3:
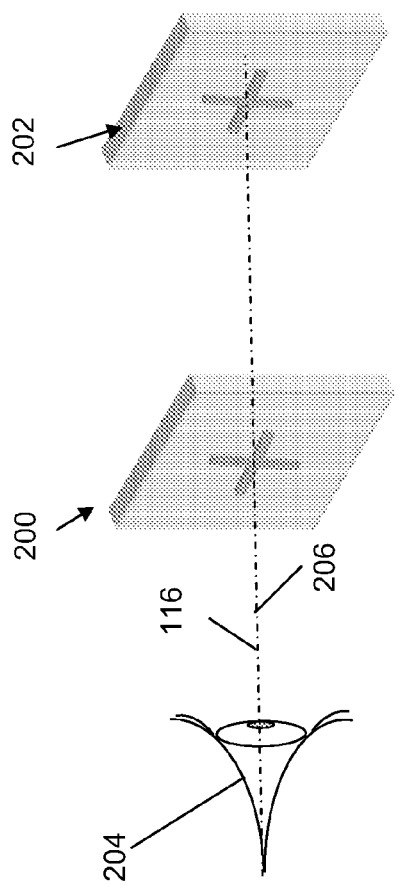

In this example, the first and second marker images 200, 202 are cross-hairs. However, as noted above, the first and second marker images can have different visual appearances, for example circles of different diameter. Consequently, in an alternative field of view 212 (FIG. 2), the circles are spatially separated or non-concentric when the first axis 206 is mis-aligned with respect to the optical receiving axis 116, but concentric when the first axis 206 is aligned with the optical receiving axis 116 (FIG. 3).

As mentioned above, the visual appearance of the first and second alignment marker images 200, 202 can differ from the cross-hairs or circles described above. In this respect, it can be desirable for the visual appearance of the first and second alignment marker images 200, 202 to have alternative forms in order to engage the interest of, for example, a child. Consequently, the first and second alignment marker images 200, 202 can be two or more pictorial images, for example one or more cartoon characters or parts thereof that combine to form a single pictorial image, such as a single cartoon character, when alignment is achieved. Indeed, the optical measurement apparatus can be made capable of permitting selection of the visual appearance(s) of the first and second alignment marker images 200, 202. Hence, it can be seen that the first and second alignment marker images 200, 202 need not completely or partially overlap to signify alignment. Instead, the optical system 100 can be configured so that the first and second alignment marker images 200, 202 appear at intended relative positions when alignment is achieved and known to the patient.

In another embodiment, the first and second display devices are disposed in a non-orthogonal relationship relative to each other, a Brewster beamsplitter (not shown) being provided to facilitate combination of the first and second alignment marker images 200, 202 in the field of view of the eye 204. This affords greater flexibility when designing the internal layout of a more compact construction for the optical measurement apparatus.

Figure 4:
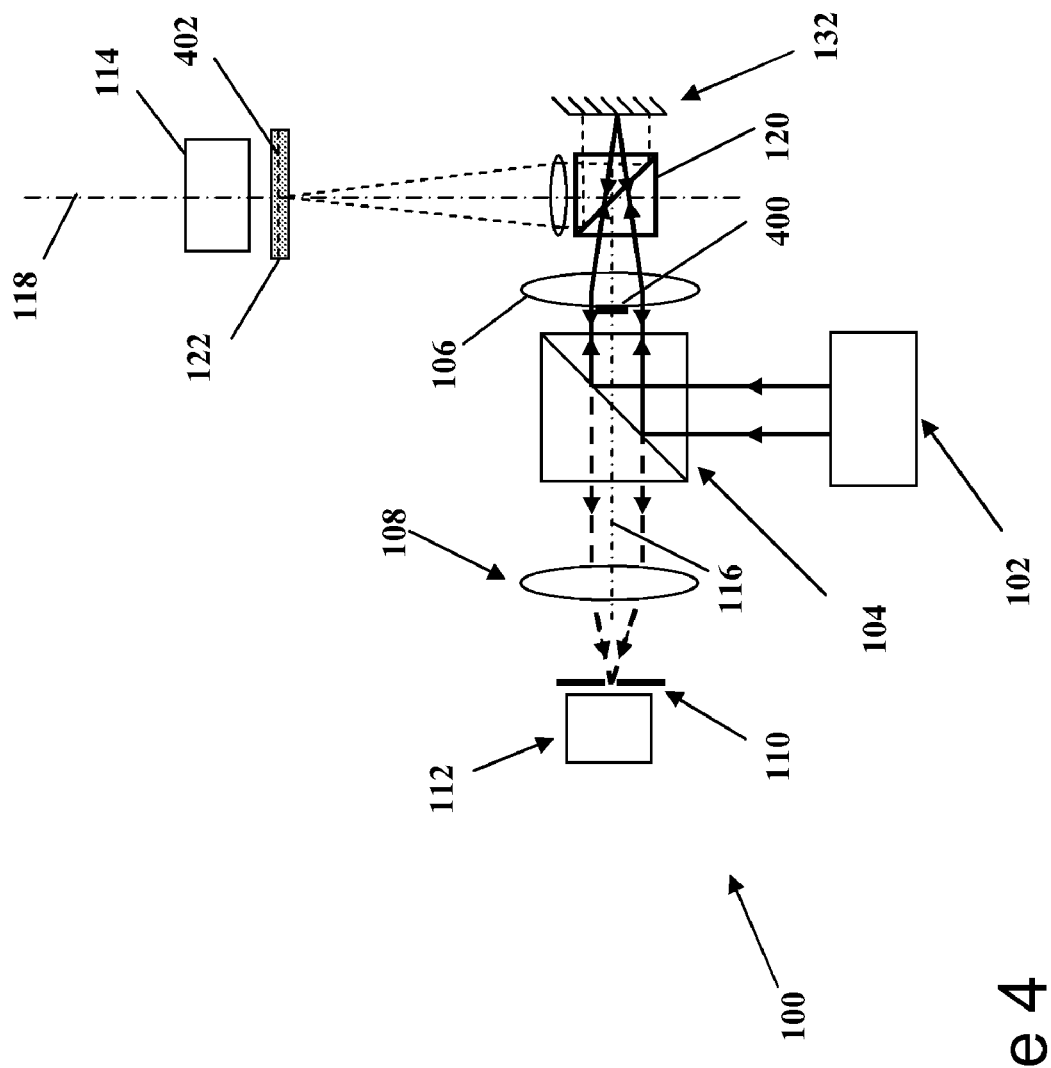
FIG. 4 is a schematic diagram of a modification to the apparatus of FIG. 1 constituting another embodiment of the invention.

In a further embodiment, the optical system 100 of FIG. 1 is modified so that the third source 124, the second graticule 128 and the third beamsplitter 126 are no longer employed. Referring to FIG. 4, a feedback element 400 is, instead, disposed co-axially with the optical receiving axis 116, for example at a central location on the scanning lens 106 and also serves, in this example, as an axial occlusion. However, the axial occlusion can be provided elsewhere in an optical path between the first source 102 and the location to be measured 132.

Hence, only one alignment marker image is employed, for example, the first alignment marker image 202. Implementation of the first alignment marker image 200 is by use of the second source 114 and the first graticule 122 of the previous embodiment bearing a pattern (not shown). Alternatively, the first source 102 typically comprises a collimating lens (not shown) adjacent to which the pattern 402 can be disposed.

Figure 5:
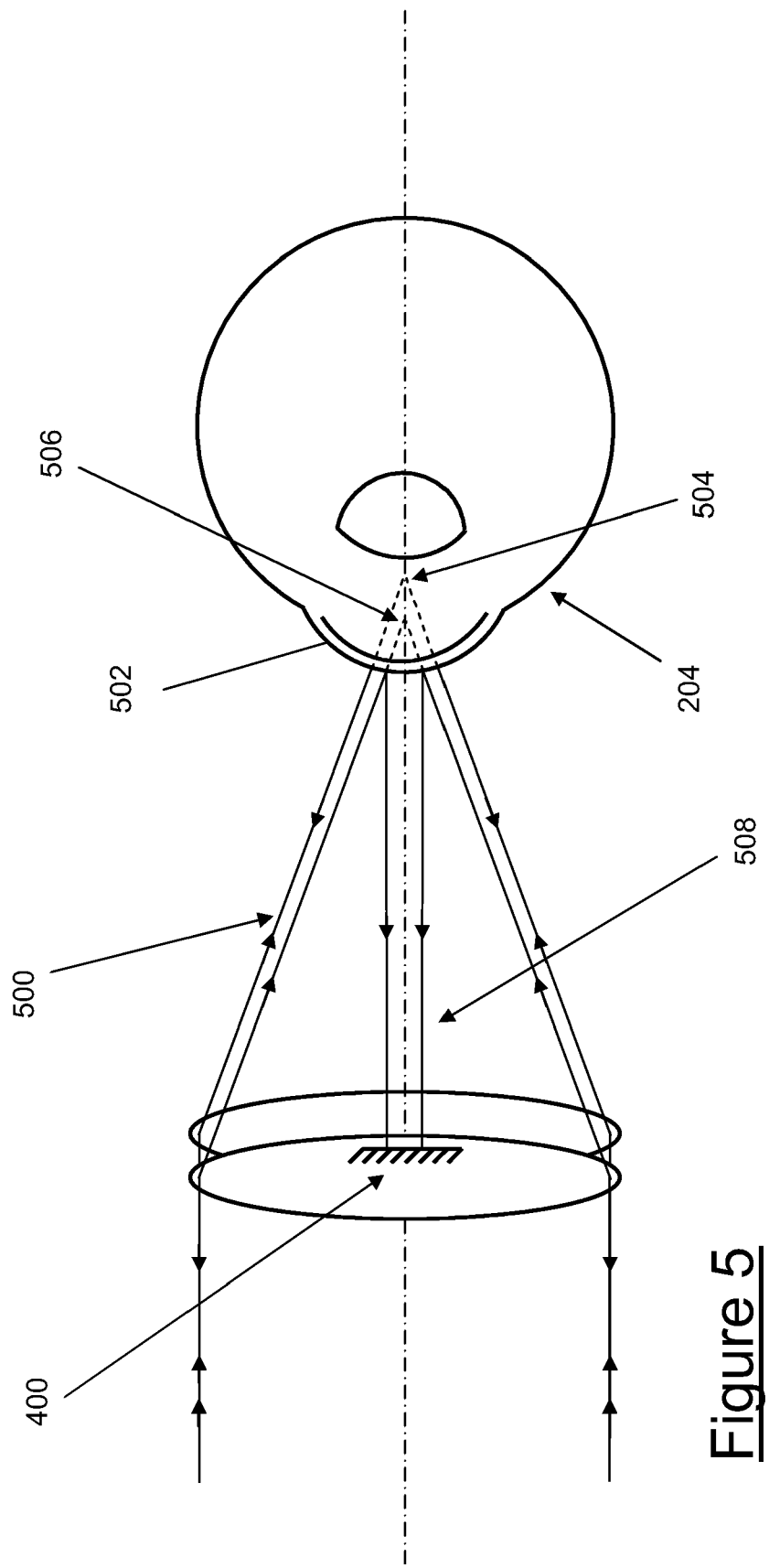
FIG. 5 is a schematic diagram of a part of the modification of the apparatus of FIG. 4 in greater detail.

In operation (FIGS. 4 and 5), and using the eye 204 as an example, the second source 114 in combination with the first graticule 122 generate an alignment beam 500 that propagates towards the location to be measured 132 in relation to the eye 204 via the second beamsplitter 120. Referring to FIG. 5, the eye 204 has an anterior corneal surface 502 and a corresponding centre of curvature 504. Additionally, the corneal surface 502 also has a reflecting focal point 506 associated therewith. If the alignment beam 500 is focussed at the centre of curvature 504 of the anterior corneal surface 502, the alignment beam 500 is retro-reflected. However, if the alignment beam 500 is focussed at the reflecting focal point 506, a collimated reflected beam 508 is achieved. The reflection is a so-called "Purkinje" reflection formed by reflection at the anterior corneal surface 502, in this example, the location to be measured.

In this example, the feedback element 400 is a mirror or other reflecting surface, though the skilled person will appreciate that other suitable optical elements can be employed, for example a phase conjugate reflector or a retro-reflector. Consequently, the Purkinje image is reflected back to the eye 204 by the feedback element 400 in order to be visible by a patient aligning their eye to the optical axis 116 of the optical system 100. The skilled person will appreciate that one of more detector elements to detect light can be employed as the element 400. The detector element(s) can feed information back to the patient or a clinician.

When the location to be measured 132 is misaligned with the optical axis 116 of the optical system 100, the collimated reflected beam 508 is off-axis with respect to the optical receiving axis 116.

As the patient aligns the location 132 on or in the eye 204 with the optical receiving axis 116 of the optical system 100, the reflected Purkinje image begins to overlap the first alignment marker image 200 in the field of view of the patient, because an axis of the reflected collimated beam 508 converges on the optical receiving axis 116. The feedback element 400 can be arranged so that the reflected Purkinje image completely overlaps the first alignment marker image 200 when complete alignment is achieved, or is offset by a predetermined amount.

Where the feedback element 400 is disposed adjacent or on the scanning lens 106, the superimposed reflected Purkinje image is brought in and out of focus as the optics, for example the scanning lens 106, moves relative to the eye 204. However, by virtue of the optics of the eye 204, the reflected Purkinje image is brought back into focus with respect to the eye 204.

The use of the Purkinje image is only one example of a reflection that can be employed in order to provide a patient with feedback concerning alignment of the location to be measured 132 in the eye 204 with the optical receiving axis 116 of the optical system 100. The Purkinje images result from reflections of diffused or collimated beams at corneal or ocular lens surfaces. However, retroflections, Fresnel reflections and collimated reflections or any other suitable reflection can be directed back to the eye 204 as a way of informing the patient of degree of alignment with the optical receiving axis 116 of the optical system 100. Indeed, reflections from other locations of the eye, for example a lens of the eye and/or a retina of the eye, can also be used to determine degree of alignment.

By controlling separation of the first alignment marker image 200 and the Purkinje image (or other reflected image), for example by specifying one or more radii of curvature of reflecting surfaces in the optical system 100, the z-separation or so called "working distance" between the first alignment marker image 200 and the Purkinje image can be controlled. In particular, this can be achieved, for example, by specifying the radius of curvature of the scanning lens 106 such that a desired z-separation is achieved, thereby controlling sensitivity of movement of one or more reflections. Furthermore, where multiple reflecting surfaces are employed, different degrees of sensitivity can be achieved. In this respect, a number of foci can be obtained, depending upon the number of alignment marker images used, which result in concentric images being seen by the eye 204, when the location to be measured 132 is aligned with the optical receiving axis 116 of the optical system 100. It should be noted that, whilst the radius of curvature of the surface of the scanning lens 106 can be used to control the z-separation mentioned above, a reflecting surface of different radius of curvature can be disposed in front of or behind the scanning lens 106 to achieve the same aim.

In another embodiment, a lens (not shown), for example a meniscus lens, a concave lens and/or a convex lens, is disposed in the optical system 100 so as to be located in an optical path between the anterior corneal surface 502 or other location to the measured 132 and the feedback element 400. In operation, a proportion of the reflected collimated beam 508 from the anterior corneal surface 502 passes through the meniscus lens and is reflected back to the eye 204 by the feedback element 400. A remaining portion of the reflected collimated beam 508 is reflected back to the eye 204 by a surface of the meniscus lens resulting in a focussed reflected beam being incident upon the eye 204. Hence, in addition to the first alignment marker image 200, the eye 204 sees two reflections: one originating from the feedback element 400 and another one as a result of the focussed reflected beam that is more sensitive to misalignment of the location to be measured 132 than the reflected beam from the feedback element 400. Consequently, the reflected image attributable to the meniscus lens moves faster than the reflection from the feedback element 400, thereby providing coarse and fine alignment indications to the patient.

Figure 6:
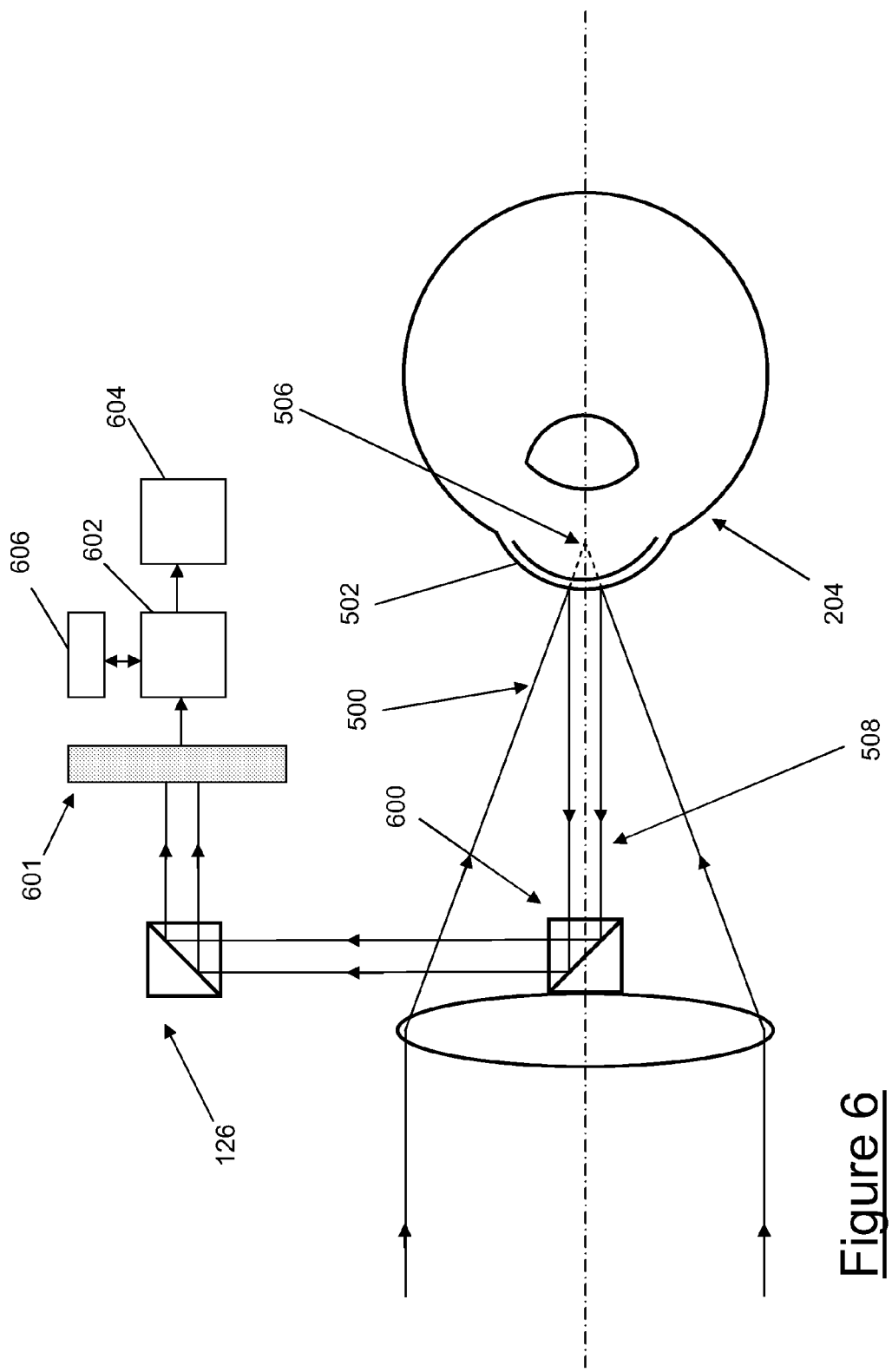
FIG. 6 is a schematic diagram of a modification to the part of the apparatus of FIG. 5 constituting a further embodiment of the invention.

In another embodiment (FIG. 6), the embodiment of FIG. 4 is modified insofar as a turning mirror 600 is disposed in a path of the reflection from the location to be measured 132 and a detector device 601 is disposed in the tangential alignment axis 118. The detector device 601 is, in this example, a Charge Coupled Device (CCD). However, the skilled person will appreciate that any other suitable imaging device can be employed, for example a digital camera, such as a so-called "webcam", a position sensitive detector or a quadrature detector. A processing resource, for example, a microprocessor 602 is coupled to the detector device 601, the processor 602 also being operably coupled to an output device 604 and a storage device 606, for example a non-volatile memory device, such as an Electronically Erasable Programmable Read Only Memory (EEPROM). Although not shown, the processor 602 can be coupled to the output device 604 via a controller module and/or interface module.

The processor 602 implements software that analyses an output signal that results from stimulation of the detector device 601 by light incident thereupon in order to determine a degree of misalignment, if any, of the location to be measured 132 with respect to the optical receiving axis 116 of the optical system 100.

In operation, the alignment beam 500 is reflected by the anterior corneal surface 502 of the eye 204 and the resultant collimated reflected beam 508 is directed by the turning mirror 600 and the third beamsplitter 126 to the detector device 601. The resultant collimated reflected beam 508 is therefore incident upon the detector device 601. The detector device 601 responds to the incident collimated reflected beam by generating the output signal in an analogous manner to that previously mentioned, the output signal being received by the processor 602 and subjected to signal processing in order to determine the degree of misalignment of the location to the measured 132 with the optical receiving axis 116 of the optical system 100.

In this respect, the processor 602 has access to spatial profile data stored in the storage device 606 indicative of elements of the detector device 601 that need to be illuminated and, if required minimum signal levels associated therewith, that correspond to receipt of the reflected collimated beam 508 in a substantially on-axis manner. The output signal therefore has a spatial profile that is compared to the stored spatial profile data, by the processor 602 in order to determine the degree of alignment mentioned above. The spatial profile is data indicating which elements of the detector device 601 are illuminated. If desired, a converse approach can be taken to determining alignment, the stored data corresponding to one or more states of misalignment. Furthermore, instead of using empirically derived spatial profile data, the spatial profile data can be modelled and generated in real or near-real time. For some types of measurement, it can be desirable for the processor 602 to measure different characteristics of the illumination of the detector device 601, the correlation between the different measured characteristics and alignment having different sensitivities. The different characteristics can be quantitative and/or qualitative.

In any event, once the degree of alignment has been calculated, it is then mapped, in this example onto a scale, for example between 1 and 10, and provided to the output device 604 as feedback information. Of course, the degree of alignment calculated or other related output data of the processor 602 can be provided to the output device 604 so as to constitute the feedback information.

The feedback information is then communicated to the patient, in this example, as an audible signal or a visual feedback, for example an animated bar indicting strength of alignment. The visual feedback can be provided by way of a display device (not shown) integrated into the optical system 100 so that the graphical feedback is visible to the eye 204. In an alternative embodiment, the first alignment marker image 200 or pattern is also generated by the display device, for example an LCD device, the display device being disposed, for example, in place of the first graticule 122 or between the first source 102 and the first beamsplitter 104 or between the first beamsplitter 104 and the second beamsplitter 120. Of course, the skilled person will appreciate that feedback information can be presented not only as an audible signal or visual feedback, but as any suitable sensory feedback appropriate for the patient. In some embodiments, the feedback information can be used by a clinician.

In the above examples relating to the provision of feedback information, the first source 102, as mentioned above, generates the measurement probe beam (not shown) that is reflected by the location to be measured 132 during measurement, the detector 112 receiving the reflected measurement probe beam. In some embodiments, the measurement probe beam also serves as the alignment beam 500.

It should, of course, be appreciated that alignment can be measured with respect to any predetermined axis of the optical system 100 and the location to be measured 132, the location to be measured not necessarily being related to the eye. Further, the alignment of the location to be measured can be achieved indirectly through misalignment of another axis associated with a body part comprising the location to be measured, for example visual and optical axes of an eye: intentional and specific misalignment with one results in alignment with the other.

Figure 7:
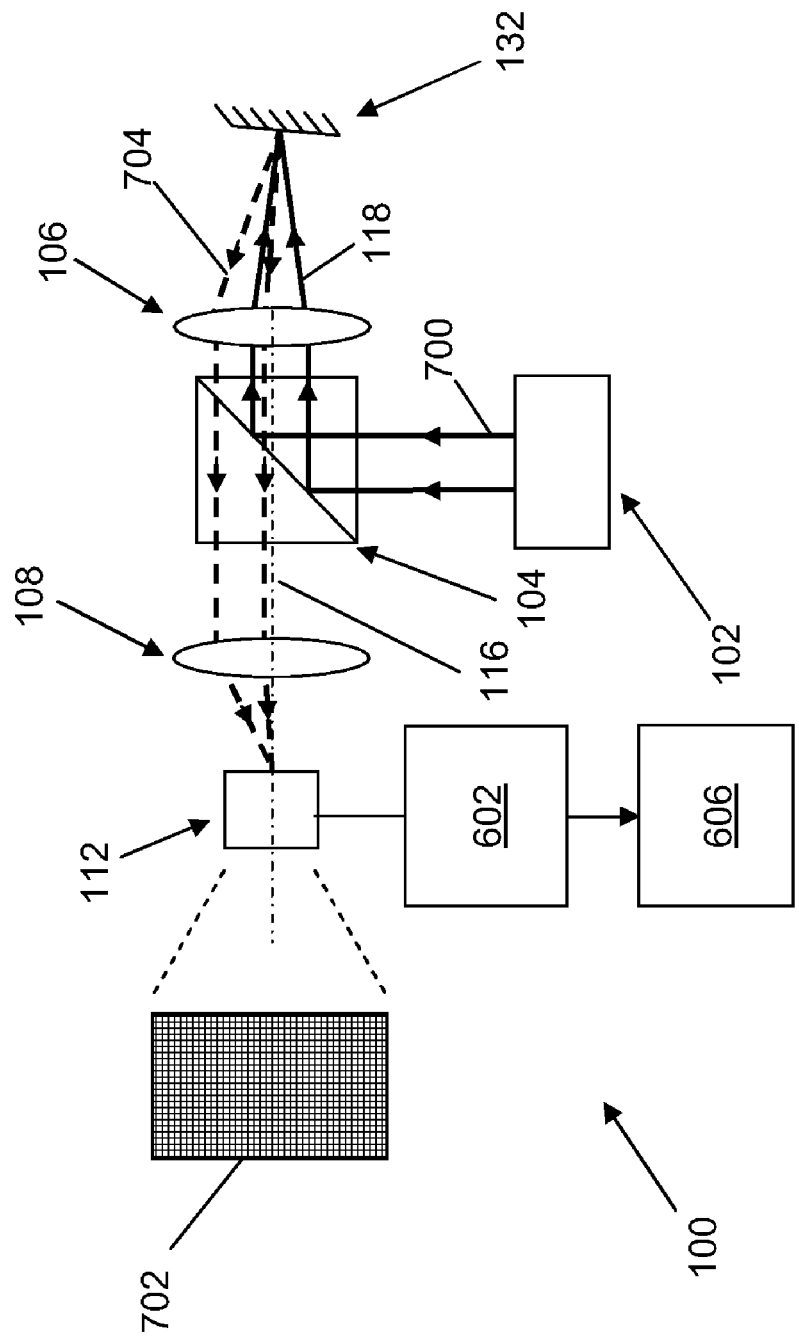
FIG. 7 is a schematic diagram of an apparatus constituting yet another embodiment of the invention.

Turning to FIG. 7, in another embodiment, the first alignment marker image 200 or the second alignment marker image 202 need not be used to determine alignment. Consequently, the second beamsplitter 120, the third beamsplitter 126, the second focussing lens 130, the first and second graticules 122, 128 and the second and third sources 114, 124 of FIG. 1 are not employed. Instead, reflections of a measurement probe beam 700, the beam used to make measurements in relation to the location to be measured 132, are employed to determine alignment or misalignment. In order to use the measurement probe beam 700 to determine a degree of alignment, the detector 112 comprises a plurality of detector elements 702 arranged as an array, for example an array of Charge Couple Devices (CCDs), Complementary Metal Oxide (CMOS) detectors, photodiodes, or a scanning point detector, for example a so-called "Nipkov disc". The detector 112 can be any suitable detector capable of translating electromagnetic radiation into electrical energy. Although not shown in this example, the detector 112 can be coupled, when required, to any suitable signal processing module, for example an analogue-to-digital converter and/or a spectral analysis module.

The optical system 100 is confocal. However, the aperture 110 is not employed. Instead, the processor 602 is employed as a Digital Signal Processor (DSP), the processor 602 being coupled to the detector 112 and suitably programmed to perform the function of the aperture 110 using one or more digital signal processing techniques.

In operation, the measurement probe beam 700 is incident upon the location to be measured 132. However, due to misalignment of the location to be measured 132 with the optical receiving axis 116 of the optical system 100, a reflection of the measurement probe beam 702 results in a reflected probe beam 704 that deviates from the optical receiving axis 116, resulting in an off-axis reflection. The reflected probe beam 704 is focussed by the first focussing lens 108 onto the plurality of detector elements 702 of the detector 112.

A number of the plurality of detector elements 702 is illuminated by the focussed reflected probe beam 704, the quantity and location of the plurality of detector elements 702 illuminated depending upon the degree of deviation of the reflected probe beam 704 from the optical receiving axis 116 of the optical system 100.

In this example, the processor 602 identifies the number of the plurality of detector elements 702 illuminated by the focussed reflected probe beam 704. Thereafter, the processor 602 selects one or more of the number of the plurality of detector elements 702 identified based upon a predetermined criterion. In this example, the criterion is discrete illumination, for example whether an element is illuminated or not illuminated. The processor 602 compares the identities of the detector elements illuminated with aligned illumination data stored by the storage device 606 identifying those elements of the plurality of detector elements 702 that are illuminated when alignment of the location to be measured 132 with the optical receiving axis 116 is substantially achieved. Consequently, the degree of misalignment, if any, can be determined by comparison of the identities of the illuminated detector elements with the stored aligned illumination data.

Other criterion can additionally be used to facilitate calculation of degree of alignment (or misalignment), for example change of illumination with time, or luminous intensity, such as maximum luminous intensity. In respect of the former criterion, knowledge of change of illumination of detector elements with time provide an indication of movement of the location to be measured 132 with respect to the optical receiving axis 116 and hence convergence upon or divergence from an aligned state. This information can be used by the processor 602 to anticipate future illuminations of detector elements 702 with the progression of time and hence optimise processing of measured detector element illumination data.

Additionally or alternatively, in relation to the criterion being luminous intensity, one or more of the detector elements 702 can nevertheless be selected based upon this criterion for signal processing purposes, for example detector elements exposed to luminous intensities above a predetermined luminous intensity threshold are selected. Output signal(s) generated by the selected one or more detector elements 702 are then subjected to a processing algorithm to perform the function previously performed by the absent aperture 110, for example selecting a number of the illuminated detector elements neighbouring a detector element corresponding to a highest luminous intensity, such as so-called "nearest neighbours".

Although the above-described technique is more processing intensive than for confocal optical systems employing the aperture 110, the use of the apertureless detector 112 in conjunction with the processor 602 enables off-axis reflections of the measurement probe beam 700 to be used when the reflected probe beam 704 would otherwise be lost due to numerical aperture limitations of the optical system 100, thereby compensating for off-axis reflections.

Figure 8:
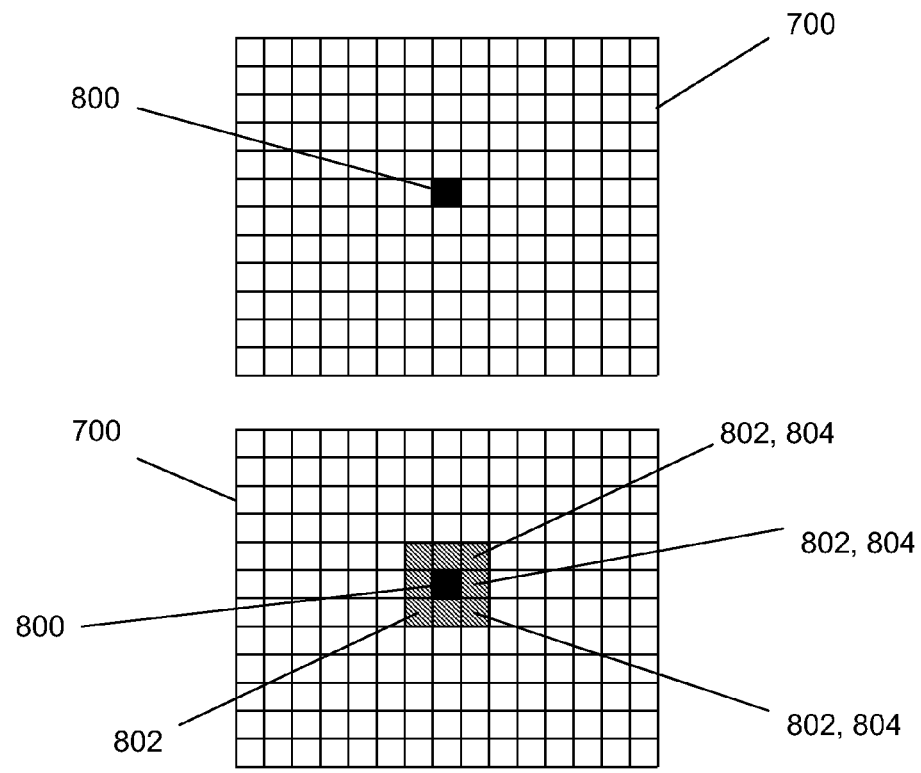
FIG. 8 is a schematic diagram of an array of detector elements.

In another example (FIG. 8), an initial number (one or more) 800 of the plurality of detector elements 702 are selected based upon the luminous intensity criterion mentioned above. The processor 602 then examines detector elements neighbouring 802 the initial number 800 of the plurality of detector elements 702 selected. Of the neighbouring elements 802 examined, the processor 602 selects detector elements in accordance with an optimised-output selection algorithm, for example adjacent detector elements, and evaluates the output signals attributable to the initial number 800 of the plurality of detector elements 702 and the adjacent detector elements selected 804 based on intensity, an intensity threshold, an intensity distribution of light received by the detector elements or any other suitable criterion. In this example, the evaluation is a calculation of an integral value, though other calculations can be performed, for example spatially averaging over the selected adjacent detector elements. If the integrated output signal calculated exceeds an integrated output signal resulting from the initial number 800 of the plurality of detector elements 702 above, then the processor 602 determines that either the location to be measured 132 is misaligned with the optical receiving axis 116 or some other signal loss is being experienced. This determination can then be communicated to the patient or a clinician as a sensory feedback indication.

In any of the above-described alignment techniques, the skilled person should appreciate that one eye can be used for alignment and another eye for measurement. Alternatively, both eyes can be used for alignment purposes, thereby improving comfort to the subject and hence reduce the motion in the eye.

It should be appreciated that references herein to "light", other that where expressly stated otherwise, are intended as references relating to the optical range of the electromagnetic spectrum, for example, between about 350 nm and about 2000 nm, such as between about 550 nm and about 1400 nm or between about 600 nm and about 1000 nm.

It should also be appreciated that the optical system 100 need not be implemented in free space and can be implemented in accordance with a waveguide type design, for example a fibre-optic type design. In this respect, a waveguide arrangement can comprise at least part of the optical system 100.

Although the above examples have predominantly been described in the context of the human eye, the skilled person will appreciate that the techniques described herein can be employed, where the context permits, in relation to measurement of any reflecting surface, for example any part of a body, be it human or otherwise. Likewise, measurement of physiological parameters can be made using the above techniques in relation to the body. One example of the physiological parameter is a blood-glucose concentration.

The optical measurement apparatus can be provided as a portable apparatus for personal or clinical use, for example a hand-held device, or table, desk or bench-top apparatus for a clinical environment where a clinician can be present.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example, microwave or infrared. The series of computer instructions can constitute all or part of the functionality described above, and can also be stored in any memory device, volatile or non-volatile, such as semiconductor, magnetic, optical or other memory device.

What is claimed is:
1. A confocal measurement apparatus comprising:
an optical system comprising:
a source arranged to emit, when in use, a probe beam, the optical system being arranged to direct, when in use, the probe beam to a location to be measured;
an apertureless detector arrangement capable of receiving a reflected beam from the location to be measured, the apertureless detector arrangement comprising a plurality of detector elements; and
a processing resource operably coupled to the apertureless detector arrangement; wherein
the processing resource is arranged to identify, when in use, a number of the plurality of detector elements illuminated by the reflected beam and select a detector element from the number of the plurality of detector elements based upon a predetermined criterion for performing a calculation in relation to an output signal generated by the selected detector element.

2. An optical measurement apparatus comprising:
an optical system comprising:
a source arranged to generate, when in use, a beam of electromagnetic radiation, the optical system being arranged to direct, when in use, the beam of electromagnetic radiation to a location to be measured; and
a feedback arrangement arranged to receive, when in use, a reflected beam from the location to be measured and to provide feedback information in response to receipt of the reflected beam, the feedback information being indicative of degree of alignment of the location to be measured with the optical system; wherein
the location to be measured is a location of a feature of an eye;
the optical system is arranged to receive the reflected beam from the eye; and
the optical system is further arranged to direct at least part of the reflected beam back to the eye, the redirected reflected beam constituting the feedback information.

3. An apparatus as claimed in claim 2, wherein the beam of electromagnetic radiation comprises an alignment image, the reflected beam also comprising the alignment image.

4. An apparatus as claimed in claim 2, wherein the reflected image originates from a part of the eye selected from one of the following parts: a cornea of the eye, a lens of the eye and/or a retina of the eye.

5. An apparatus as claimed in claim 2, wherein the optical source is arranged to generate a plurality of images with respect to a vanishing point, the optical system being further arranged to direct, when in use, the plurality of images to the eye for alignment thereof.

6. An apparatus as claimed in claim 5, wherein the feedback arrangement comprises a processing resource operably coupled to an image capture device in order to generate the feedback information in response to receipt of the reflected beam relative to a predetermined axis, the predetermined axis corresponding to an aligned state.

7. An apparatus as claimed in claim 6, wherein:
the location to be measured is a location of a feature of an eye; and
the feedback arrangement is arranged to determine, when in use, a location of the feature of the eye relative to the optical system.

8. An apparatus as claimed in claim 7, wherein:
the optical system has a receiving axis constituting the predetermined axis; and
the processing resource is arranged to provide the feedback information as an indication of the degree of alignment of the location of the feature of the eye with the receiving axis.

9. An apparatus as claimed in claim 2, wherein:
the feedback arrangement comprises a processing resource operably coupled to an image capture device;
the optical system has a receiving axis;
the location to be measured is coaxial with a first axis of an eye, the eye having a second axis; and
the processing resource is arranged to provide feedback for obtaining a misalignment of the first axis with the receiving axis in order to achieve alignment of the second axis with the receiving axis.

10. An apparatus as claimed in claim 2, wherein the feedback information is an audible or visual indication of alignment.

11. An apparatus as claimed in claim 2, wherein the source is capable of emitting a measurement probe beam invisible to an eye.

12. An apparatus as claimed in claim 2, wherein:
the source is arranged to generate a measurement probe beam, the optical system being arranged to direct, when in use, the measurement probe beam to the location to be measured; and further comprising
a detector arranged to receive, when in use, a reflected measurement probe beam from the location to be measured.

13. An apparatus as claimed in claim 12, wherein the measurement probe beam also serves as the beam of electromagnetic radiation.

14. An apparatus as claimed in claim 2, wherein the feedback arrangement comprises a processing resource operably coupled to an image capture device, the processing resource being arranged to generate a first measure of a first characteristic corresponding to illumination of the image capture device, the first measure constituting the feedback information.

15. An apparatus as claimed in claim 14, wherein the processing resource is arranged to generate a second measure of a second characteristic corresponding to illumination of the image capture device, the second measure being of a different type to the first measure.

16. An apparatus as claimed in claim 2, further comprising a store for storing characteristic data relating to illumination and corresponding to a state of substantially optimum alignment with the optical system or a state of mis-alignment with the optical system.

17. An apparatus as claimed in claim 16, wherein the processing resource is arranged to compare the feedback information with the characteristic data stored in order to determine alignment or misalignment of the location to be measured with the optical system.

* * * * *